(12) United States Patent
Read et al.

(10) Patent No.: US 9,500,546 B2
(45) Date of Patent: Nov. 22, 2016

(54) IMPACT DETECTION AND ACOUSTIC EMISSION DATA PROCESSING

(75) Inventors: Ian James Read, Bristol (GB); Ryan Nichols John, Bristol (GB); William Neil MacPherson, Scotland (GB)

(73) Assignee: BAE SYSTEMS plc, London (GB)

( * ) Notice: Subject to any disclaimer, the term of this patent is extended or adjusted under 35 U.S.C. 154(b) by 342 days.

(21) Appl. No.: 14/240,237

(22) PCT Filed: Aug. 21, 2012

(86) PCT No.: PCT/GB2012/052037
§ 371 (c)(1),
(2), (4) Date: Feb. 21, 2014

(87) PCT Pub. No.: WO2013/027046
PCT Pub. Date: Feb. 28, 2013

(65) Prior Publication Data
US 2014/0202248 A1    Jul. 24, 2014

(30) Foreign Application Priority Data
Aug. 22, 2011 (GB) .................................. 1114418.5

(51) Int. Cl.
*G01L 5/00* (2006.01)
*G01N 29/11* (2006.01)
(Continued)

(52) U.S. Cl.
CPC ............. *G01L 5/0052* (2013.01); *G01N 29/11* (2013.01); *G01N 29/14* (2013.01);
(Continued)

(58) Field of Classification Search
CPC .. G01N 29/11; G01N 29/14; G01N 29/4427; G01N 29/48; G01N 2291/0231; G01N 2291/0289; G01N 2291/2694; G01L 5/0052
USPC .......................................................... 73/583
See application file for complete search history.

(56) References Cited

U.S. PATENT DOCUMENTS 5,806,796 A * 9/1998 Healey ................ B29C 44/1233
244/117 R
6,591,681 B1 * 7/2003 Shimada .............. G01N 29/045
73/600

(Continued)

FOREIGN PATENT DOCUMENTS

DE    19701405 A1    7/1998
WO    2010052393 A1    5/2010
WO    2013027046 A1    2/2013

OTHER PUBLICATIONS

International Preliminary Report on Patentability and Written Opinion of The International Searching Authority for Patent Application No. PCT/GB2012/052037, mailed on Mar. 6, 2014, 8 pages.

(Continued)

*Primary Examiner* — J M Saint Surin
(74) *Attorney, Agent, or Firm* — Finch & Maloney PLLC

(57) ABSTRACT

A method and apparatus for processing measurements of an acoustic wave, the acoustic wave being within a member (12) made of a composite material and caused by an impact to the member (12), the method comprising: analyzing the measurements to detect an initial acoustic wave feature; analyzing the measurements to detect the presence of further acoustic wave features, the further features occurring after the initial feature; if there are no further acoustic wave features, determining that the impact to the member (12) has not changed the structure of the member (12); if there are further features, determining a value of a function of the further acoustic wave features; if the determined value satisfies certain criteria, determining that the impact has changed the structure of the member (12); and if the determined value does not satisfy the criteria, determining that the impact has not changed the structure of the member (12). By doing so, impact induced damage is detected and quantified by processing separately acoustic data generated by the impact from acoustic data generated by acoustic emission due to damage generation.

20 Claims, 5 Drawing Sheets

(51) Int. Cl.
*G01N 29/14* (2006.01)
*G01N 29/44* (2006.01)
*G01N 29/48* (2006.01)

(52) U.S. Cl.
CPC ......... *G01N 29/4427* (2013.01); *G01N 29/48* (2013.01); *G01N 2291/0231* (2013.01); *G01N 2291/0289* (2013.01); *G01N 2291/2694* (2013.01)

(56) References Cited

U.S. PATENT DOCUMENTS

| | | | | |
|---|---|---|---|---|
| 8,670,290 B2* | 3/2014 | Aklil | | 367/125 |
| 2010/0050777 A1* | 3/2010 | Zheng | | G01L 9/0058 73/727 |
| 2011/0030537 A1 | 2/2011 | Mullen | | |
| 2011/0112775 A1 | 5/2011 | Bramban | | |
| 2014/0165728 A1* | 6/2014 | Chaume | | G01N 29/045 73/584 |
| 2014/0260527 A1* | 9/2014 | Mazzeo | | G01N 29/045 73/12.05 |

OTHER PUBLICATIONS

International Search Report received for Patent Application No. PCT/GB2012/052037, mailed on Feb. 11, 2012, 5 pages.
GB Intellectual Property Office Search Report under Section 17(5) received for GB Patent Application No. 1114418.5, mailed Nov. 22, 2011, 3 pages.
Hayward, et al., "An automatic impact monitor for a composite panel employing smart sensor technology," Institute of Physics Publishing, Smart Mater. Struct. 14 (2005), pp. 265-271.
Sultan, et al., "On impact damage detection and quantification for CFRP laminates using structural response data only," Mechanical Systems and Signal Processing, Elsevier, vol. 25, (2011), pp. 3135-3152.
Staszewski, W.J., "Damage Detection in Composite Materials Using Optical Fibres—Recent Advances in Signal Processing," Smart Structures and Materials 2000: Smart Structures and Integrated Systems, Norman M. Wereley, Editor, Proceedings of SPIE, vol. 3985 (2000), pp. 261-270.

* cited by examiner

IMPACT DETECTION AND ACOUSTIC EMISSION DATA PROCESSING

FIELD OF THE INVENTION

The present invention relates to processing measurements of acoustic waves. In particular, the present invention relates to processing measurements of an acoustic wave within a member made of a composite material and caused, at least in part, by an impact to the member.

BACKGROUND

Laminated composites are widely used on aircraft, e.g. as fuselage or wing skins, because of their low mass and adaptable properties.

Impacts to composite structures can weaken such structures. Low velocity impacts typically leave little visible sign that an impact has occurred.

For example, composite delamination tends to significantly reduce structural integrity of a composite structure, but there may be no external signs of damage.

Manual inspection techniques to detect such damage are typically costly, time consuming and risk overlooking damaged areas.

SUMMARY OF THE INVENTION

In a first aspect, the present invention provides a method of processing measurements of an acoustic wave, the acoustic wave being within a member and caused, at least in part, by an impact to the member, the member being made of a composite material, the method comprising: analysing the measurements of the acoustic wave to detect an initial acoustic wave feature in the measured acoustic wave; analysing the measurements of the acoustic wave to determine whether or not there is one or more further acoustic wave features present in the measured acoustic wave, each of the one or more further acoustic wave features occurring in the acoustic wave after the occurrence of the initial acoustic wave feature; if there are no further acoustic wave features present in the measured acoustic wave, determining that the impact to the member has not changed the structure of that member; if there is one or more further acoustic wave features present in the measured acoustic wave, determining a value of a function of one or more of the further acoustic wave features; if the determined value satisfies one or more criteria, determining that the impact to the member has changed the structure of that member; and, if the determined value does not satisfy the one or more criteria, determining that the impact to the member has not changed the structure of that member.

The method may further comprise filtering the measurements of the acoustic wave, wherein the initial acoustic wave feature is a feature of the filtered measurements, and each of the further acoustic wave features is a feature of the filtered measurements.

The initial acoustic wave feature may be a pulse having an absolute amplitude greater than a first threshold value, and each of the further acoustic wave features may be a pulse having an absolute amplitude greater than the first threshold value.

A time period between the initial acoustic wave feature occurring in the measured acoustic wave and each of the further acoustic wave features occurring in the measured acoustic wave may be greater than a first threshold time-period.

A time period between the initial acoustic wave feature occurring in the measured acoustic wave and each of the further acoustic wave features occurring in the measured acoustic wave may be less than or equal to a second threshold time-period.

The function of one or more of the further acoustic wave features may be the ratio between an amplitude of the initial acoustic wave feature and an amplitude of a further acoustic wave feature.

The one or more criteria may comprise a criterion that the determined value exceeds a second threshold value.

The method may further comprise, using measurements of the acoustic wave measured at a plurality of different points on or in the member, determining a location of the impact.

The method may further comprise, if it is determined that the impact to the member has changed the structure of that member, outputting an indication that the structure of the member has changed.

The method may be performed, at least in part, on an unmanned aircraft.

In a further aspect, the present invention provides apparatus for use with a member, the member being made of a composite material, the apparatus comprising: a sensor arranged to measure an acoustic wave, the acoustic wave being within a member and caused by an impact to the member; and one or more processors arranged to: analyse the measurements of the acoustic wave to detect an initial acoustic wave feature in the measured acoustic wave; analyse the measurements of the acoustic wave to determine whether or not there is one or more further acoustic wave features present in the measured acoustic wave; if there are no further acoustic wave features present in the measured acoustic wave, determine that the impact to the member has not changed the structure of that member; if there is one or more further acoustic wave features present in the measured acoustic wave, determine a value of a function of one or more of the further acoustic wave features; if the determined value satisfies one or more criteria, determine that the impact to the member has changed the structure of that member; and if the determined value does not satisfy the one or more criteria, determine that the impact to the member has not changed the structure of that member.

The sensor may be either a piezoelectric sensor or a fibre optic sensor.

The sensor may be either bonded to the member or embedded into the member.

In a further aspect, the present invention provides an unmanned aircraft comprising apparatus according to the above aspect, and the member.

In a further aspect, the present invention provides a program or plurality of programs arranged such that when executed by a computer system or one or more processors it/they cause the computer system or the one or more processors to operate in accordance with the method of any of the above aspects.

In a further aspect, the present invention provides a machine readable storage medium storing a program or at least one of the plurality of programs according to the above aspect.

DETAILED DESCRIPTION

Figure 1:
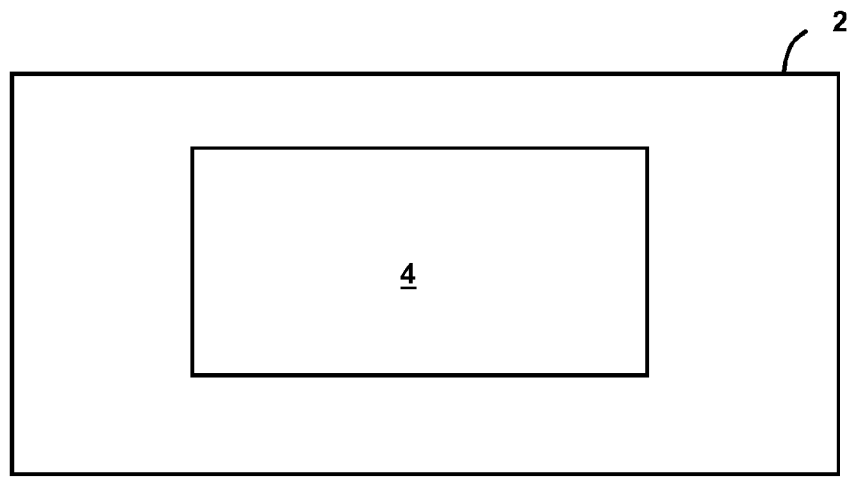
FIG. 1 is a schematic illustration (not to scale) of an example of an aircraft in which an embodiment of a detector for detecting impacts to a portion of the aircraft and discriminating between damaging and non-damaging impacts is implemented.

FIG. 1 is a schematic illustration (not to scale) of an example of an aircraft 2.

In this example, the aircraft 2 comprises a detector 4 for detecting impacts to a portion of the aircraft 2 and discriminating between damaging and non-damaging impacts.

An embodiment of the detector 4 is described in more detail later below with reference to FIG. 2.

An impact to the aircraft 2 may occur whilst the aircraft 2 is in operation, e.g. a bird or debris impacting the aircraft 2, or whilst the aircraft is not in operation, e.g. an impact incurred whilst the aircraft 2 is being transported.

The terminology "damaging impact" is used herein to refer to an impact to a member (e.g. part of the aircraft 2) that adversely affects that member, e.g. an impact that changes the structure of the member such that the strength of the impacted member is reduced, or an impact that changes the structure of the member such that the ability of the impacted member to perform a certain function is impaired. Furthermore, "damage" is used herein to refer to easily visible damage, barely visible impact damage (BVID), or invisible damage.

In this example, the aircraft 2 is an unmanned aircraft.

Figure 2:
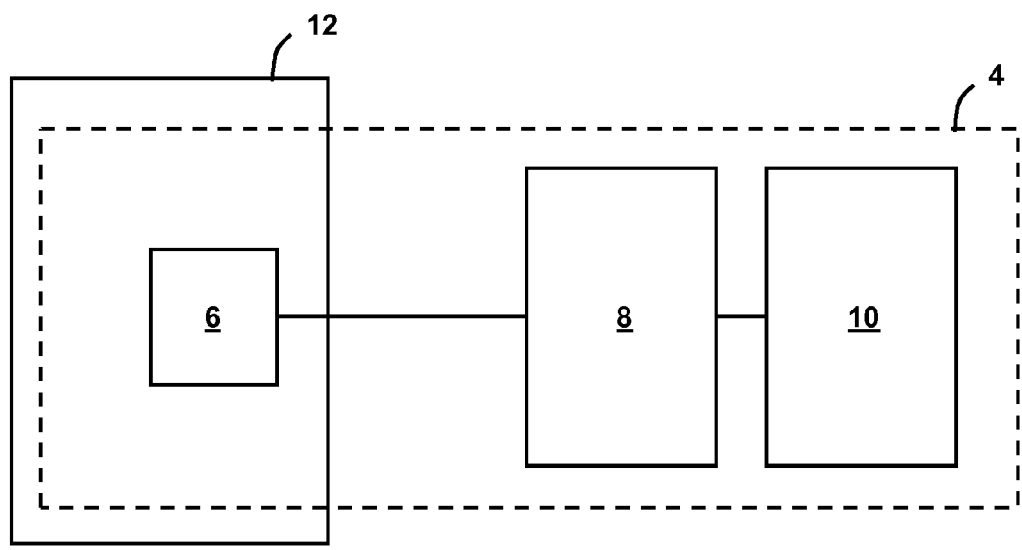
FIG. 2 is a schematic illustration (not to scale) showing an embodiment of the detector.

FIG. 2 is a schematic illustration (not to scale) showing an embodiment of the detector 4.

In this embodiment, the detector 4 comprises a sensor 6, a processor 8, and a storage device 10.

In this embodiment, the sensor 6 is a broadband, non-resonant piezoelectric sensor. In this embodiment the sensor 6 comprises a packaged Lead Zirconate Titanate (PZT) disk with a 10 mm diameter and 0.2 mm thickness. The sensor 6 is capable of detecting dynamic strain. The sensor 6 is sensitive to several hundred kilohertz.

In this embodiment, the sensor 6 is connected to the processor 8 such that, in operation, a signal is sent from the sensor 6 to the processor 8.

In this embodiment, the processor 8 is for processing (including the filtering and amplification of) signals received from the sensor 6, as described in more detail later below with reference to FIG. 3.

In this embodiment, the processor 8 is connected to the storage device 10 such that, in operation, a processed signal is sent from the processor 8 to the storage device 10.

In this embodiment, the storage device 10 is for storing signals received from the processor 8, as described in more detail later below with reference to FIG. 3.

Also shown schematically in FIG. 2 is the portion of the aircraft 2 that impacts to are to be detected. This portion of the aircraft 2 will hereinafter be referred to as "the portion" and is indicated in FIG. 2 by the reference numeral 12.

In this embodiment, the sensor 6 is bonded (e.g. using an adhesive) to a surface of the portion 12.

In this embodiment, the portion 12 is a panel made of a composite material.

In this embodiment, the portion is between 1 mm and 10 mm thick.

The terminology "composite material" is used herein to refer to a material comprising two or more separate constituent materials. These constituent materials remain separate and distinct, i.e. are distinguishable, at the macroscopic or microscopic scale within the composite material.

In this embodiment, the portion 12 is made of a composite material that comprises a matrix of some sort of strengthening material (e.g. Kevlar™, carbon fibre, glass fibre, etc.) in the form of a plurality of overlapping sheets (e.g. a woven or unidirectional cloth) which is held together by some sort of resin.

In this embodiment, the portion is made of a composite material that is suitable for use as a surface of an aircraft, i.e. a relatively lightweight composite material. For example, the portion 12 may be a panel made of glass fibre and LM100 resin, or the portion may be a panel made of monolithic carbon fibre and MTM46 resin.

The types of damage to the portion 12 that may be caused by an impact include matrix cracking, fibre break, and delamination (i.e. de-bonding) of the sheets that form the composite material.

In this embodiment, the portion 12 is positioned at a leading edge of the aircraft 2. For example, the portion 12 is a portion along a leading edge of a wing of the aircraft 2, or positioned at the nose of the aircraft 2. A leading edge of the aircraft 2 tends to be more susceptible to impact damage.

Figure 3:
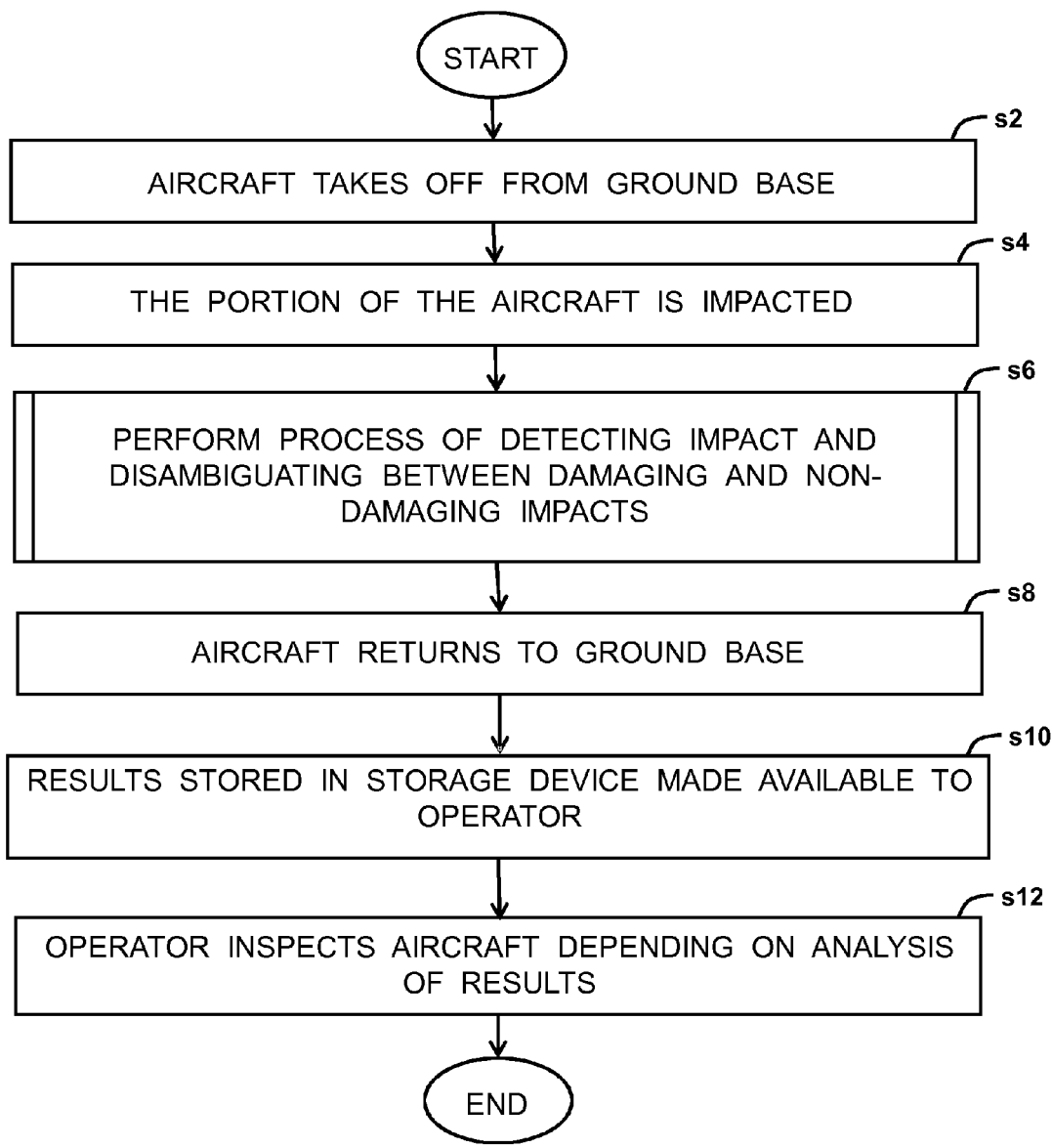
FIG. 3 is a process flow chart showing certain steps of an example of a method of operating the aircraft.

FIG. 3 is a process flow chart showing certain steps of an example of a method of operating the aircraft 2.

At step s2, the aircraft 2 is launched.

In this example, the aircraft 2 takes-off from a ground-base from which the aircraft 2 is operated by an operator.

In this example, the aircraft 2 is to complete a specified task, for example, surveillance of a target.

At step s4, the portion 12 of the aircraft is impacted, e.g. by one or more birds or pieces of debris.

At step s6, a method by which an impact to the portion 12 is detected, and by which damaging and non-damaging impacts is discriminated between is performed.

An embodiment of a method of detecting impacts to the portion 12 and discriminating between damaging and non-damaging impacts is described in more detail later below with reference to FIG. 4.

At step s8, after completing the specified task, the aircraft 2 is returned (under the control of the operator) to the ground-base from which it was launched at step s2.

At step s10, the results of the method of detecting impacts to the portion and discriminating between damaging and non-damaging impacts (performed at step s6) that are stored in the storage device 10 (as described in more detail later below with reference to FIG. 4) are made available to an operator of the aircraft 2. For example, the results stored in the storage device 10 are downloaded from the storage device 10 to a computer.

At step s12, the results made available to the operator are analysed by the operator and, depending on the analysis of the results, the operator may inspect and/or repair the portion 12, as described in more detail later below.

Thus, a method of operating the aircraft 2 is provided.

Figure 4:
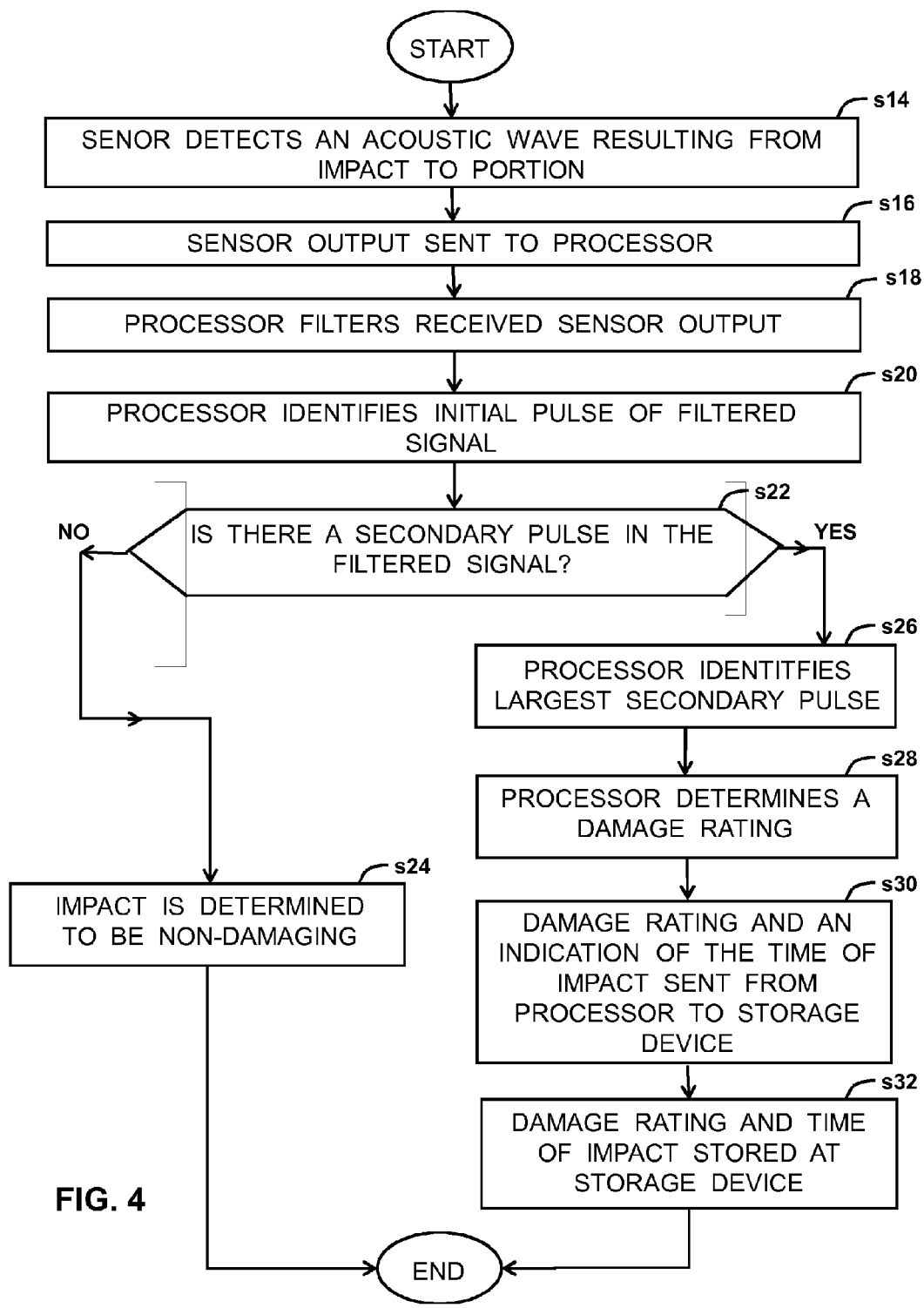
FIG. 4 is a process flow chart showing certain steps of an embodiment of a method of detecting an impact to the portion of the aircraft and discriminating between damaging and non-damaging impacts.

FIG. 4 is a process flow chart showing certain steps of an embodiment of a method of detecting an impact to the portion 12 of the aircraft 2 and discriminating between damaging and non-damaging impacts.

At step s14, the sensor 6 detects an acoustic wave caused by the impact to the portion 12.

In this embodiment, the sensor 6 measures 5 million samples per second. This sample rate (and/or the length of time a signal is measured for) may be specified depending on the size/thickness of the portion 12. For example, to facilitate the detection of impact in larger portions (i.e. in which the sensor 6 is positioned further away from the point of impact), the sample rate may be reduced to increase the signal length.

At step s16, the unprocessed sensor output is sent from the sensor 6 to the processor 8.

At step s18, the processor 6 filters the received signal. Also, at step s18, the processor 6 amplifies the received signal.

In this embodiment, the signal received from the sensor 6 is filtered using a band-pass filter. Also, the signal is filtered such that frequencies within the frequency range 50-350 kHz are passed, and frequencies outside this range are attenuated.

The use of the band-pass filter advantageously tends to improve bit resolution on the high frequency content of the signal, which is typically relatively small when compared to the large low frequency content.

At step s20, the processor 8 identifies an "initial pulse" of the filtered signal.

The terminology "initial pulse" is used herein to refer the first pulse of the filtered signal whose absolute amplitude exceeds a pre-defined threshold value.

In this embodiment, the initial pulse is identified using a conventional peak detection function.

At step s22, the processor 8 determines whether or not there is a "secondary pulse" in the filtered signal.

The terminology "secondary pulse" is used herein to refer a pulse of the filtered signal that satisfies the following criteria:
 the pulse is a different pulse to the initial pulse;
 the absolute amplitude of the pulse exceeds the pre-defined threshold value;
 the pulse occurs at a time that is between a first pre-defined time period after the initial pulse and the end of the pulse.

In this embodiment, the first pre-defined time is 1 ms.

In this embodiment, a secondary pulse is a pulse that satisfies the above mentioned criteria. However, in other embodiments, one or more different appropriate criteria may be used instead of or in addition to any of those listed above. For example, in other embodiments the criteria that the pulse occurs at a time that is between a first pre-defined time period after the initial pulse and the end of the pulse is replace by the criteria that the pulse occurs at a time that is between a first pre-defined time period after the initial pulse and a second pre-defined time period (e.g. 9 ms) after the initial pulse.

In this embodiment, a pulse occurring between the initial pulse and the first pre-defined time period after the initial pulse is deemed to be part of the initial pulse.

In this embodiment, all pulses that exceed the pre-defined threshold value that are detected within a time period of 20 ms from an initial pulse are assumed to be caused by the same impact as that which caused the initial pulse. In other words, all pulses in a signal that occur later than 20 ms after the initial pulse are assumed to be caused by a different impact event. In other embodiments, a different time period is used.

Figure 5A:
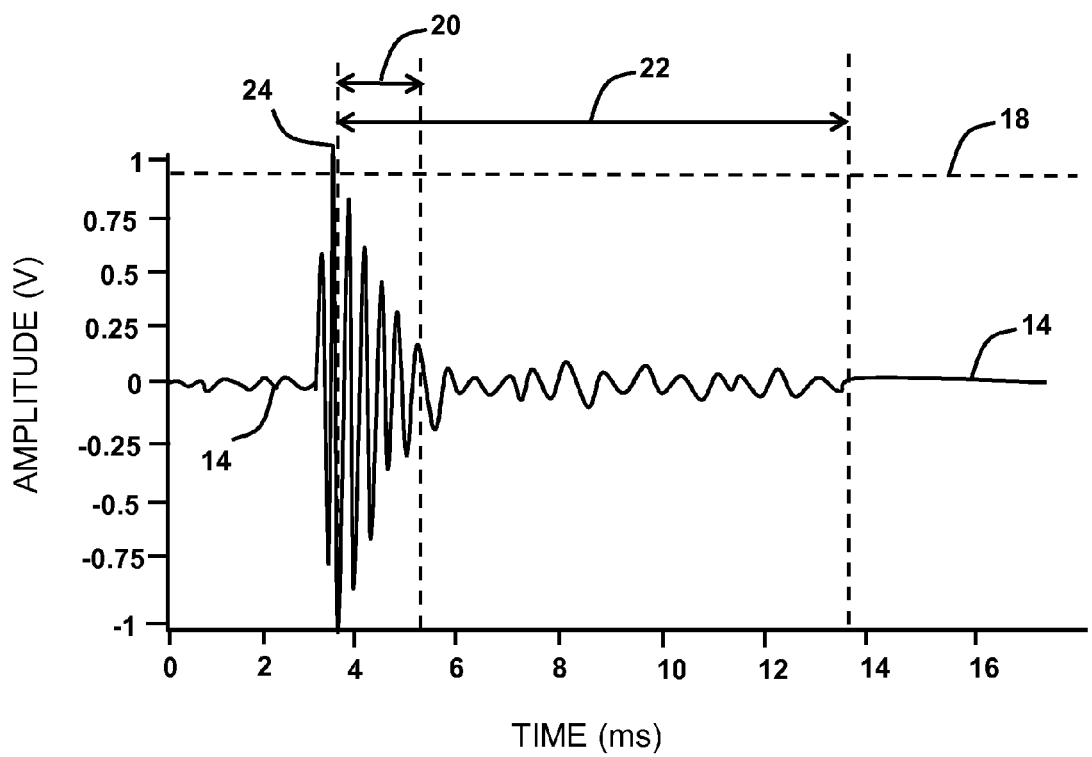
FIG. 5A is a schematic illustration (not to scale) of a first example of a filtered signal.

FIG. 5A is a schematic illustration (not to scale) of a first example of a filtered signal, hereinafter referred to as the "first signal" and indicated by the reference numeral 14.

Figure 5B:
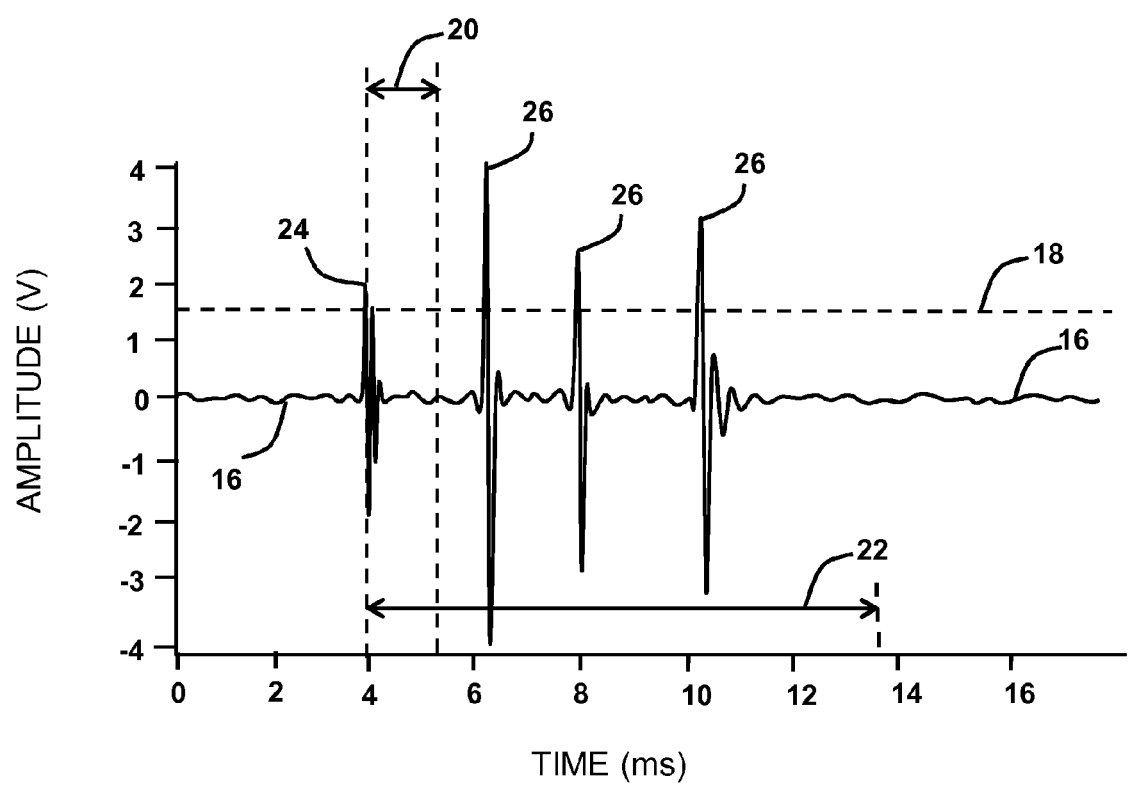
FIG. 5B is a schematic illustration (not to scale) of a second example of a filtered signal.

FIG. 5B is a schematic illustration (not to scale) of a second example of a filtered signal, hereinafter referred to as the "second signal" and indicated by the reference numeral 16.

In FIGS. 5A and 5B, the pre-defined threshold is indicated by a dotted line and the reference numeral 18.

Also, in FIGS. 5A and 5B, the first pre-defined time period after the initial pulse has elapsed is indicated by the reference numeral 20.

Also, in FIGS. 5A and 5B, a 20 ms time period after the initial pulse has elapsed is indicated by the reference numeral 22.

The initial pulses of the first signal 14 and the second signal 16 are indicated by the reference numeral 24.

The first signal 14 has no pulses that satisfy the above criteria. In other words, the first signal 14 has no secondary pulses.

Thus, for the first signal 14, at step s22, the processor 8 determines that there are no secondary pulses for that signal.

The second signal 16 has three pulses that satisfy the above criteria. In other words, the first signal 14 has three secondary pulses. These secondary pulses are each indicated in FIG. 5B by the reference numeral 26.

Thus, for the second signal 16, at step s22, the processor 8 determines that there are secondary pulses 26 for that signal.

If, at step s22, the processor 8 determines that there are no secondary pulses for the filtered signal (i.e. as determined for the first filtered signal 14), the method proceeds to step s24.

However, if, at step s22, the processor 8 determines that there are secondary pulses for the filtered signal (i.e. as determined for the second filtered signal 16), the method proceeds to step s26.

At step s24, the impact is determined to be non-damaging.

In this embodiment, non-damaging impacts are discarded and no result is output from the processor 8 to be stored at the storage device 10. In other embodiments, non-damaging impact events are treated in a different way. For example, in other embodiments, non-damaging impact events are stored at the storage device 10, but are not reported to the maintainer of the aircraft 2. These stored non-damaging impact events may be used for offline analysis.

At step s26, the largest of the secondary pulses 26 of the filtered signal, i.e. the secondary pulse 26 having the largest absolute amplitude, is identified by the processor 8.

At step s28, the processor determines a "damage rating" for the impact associated with the filtered signal.

In this embodiment, a damage rating is determined as the ratio between the absolute amplitude of the largest secondary pulse 26 of the filtered signal (that was identified at step s26) and the absolute amplitude of the initial pulse 24 of that filtered signal.

In this embodiment, the determined damage rating for a filtered signal is used to give an indication of the severity of the impact associated with that filtered signal. For example, a damage rating of less or equal to than 1.5 may indicate "not serious damage", a damage rating of between 1.5 and 2.5 may indicate "moderate damage", and a damage rating of greater than or equal to 2.5 may indicate "serious damage".

At step s30, the determined damage rating, and a time-stamp associated with the signal received by the processor 8 from the sensor 6 (i.e. a "time of impact"), is sent from the processor 8 to the storage device 10.

At step s32, the storage device 10 stores the received damage rating and time-stamp for use by the operator of the aircraft 2.

Thus, a method of detecting an impact to the portion 12 of the aircraft 2 and discriminating between damaging and non-damaging impacts is provided.

An advantage provided by the above described apparatus and method is that an impact to the portion of the aircraft can be detected. In particular, an automated impact detection capability tends to be provided. This tends to be of particular use in unmanned aircraft (or other unmanned entities) in which, in operation, there is no human present to detect an impact event and indicate to maintenance crew that such an event has occurred. In manned aircraft (or other manned entities), a human operator/passenger (e.g. a pilot) may indicate to maintenance crew that an impact event has occurred, thereby prompting inspection.

A further advantage provided by the above described apparatus and method is that damaging and non-damaging events tend to be disambiguated. By differentiating between damaging and non-damaging impacts, inspection of the aircraft can be focused on those portions for which damaging impacts were detected. This tends to reduce the costs and time spent performing inspection of the aircraft. Furthermore, this tends to reduce the risks of overlooking damaged areas during inspection.

A further advantage provided by the above described apparatus and method is that an indication of the severity of an impact event (i.e. an indication of the damage caused by an impact) is provided. An automated classification of the severity of damage is provided by the damage rating.

This damage rating can be advantageously used to aid decisions on maintenance actions, such as inspections and repairs.

The use of the above described damage rating to indicate the severity of damage advantageously tests the significance of detected secondary pulses in the filtered signal, thereby providing a measure of damage that is robust to the signal-to-noise ratio of the sensor being reduced. The signal-to-noise ratio of the sensor may be reduced, for example, if the portion being made of a highly attenuating composite material. This may cause noise to be of similar magnitude to the initial impact pulse even for lower energy non-damaging impacts.

The above described apparatus and method advantageously exploit the presence of one or more secondary pulses in the filtered signal. Such secondary signals may, for example, result from acoustic emissions during damage creation through one or more of a set of failure mechanisms of the composite material.

A further advantage provided by the above described apparatus and method is that it tends to be possible detect visible, barely visible, and invisible damage to the portion. Furthermore, an indication that this damage has occurred and the severity of this damage is provided.

A further advantage provided by the above described apparatus and method is that impacts from unknown impactors may be detected. This tends to be in contrast to conventional methods for investigating impact interactions with composite material in which instrumented impactors are typically used to determine the dynamics of the interaction.

The use of a filter to filter the signal from the sensor advantageously tends to produce identifiable features that provide a "fingerprint" for confirming damage of the composite material has occurred. Unfiltered signals tend to have few such features.

A value for the absolute amplitude threshold for determining initial and secondary pulses (i.e. the above mentioned pre-defined threshold value), a value for the first pre-defined time period, a value for second pre-defined time period, and/or a range of values of the damage rating that indicate a given severity of damage may advantageously be determined (e.g. by testing) for a piece of a given composite material of a given size and shape. Thus, the above described apparatus and method can be advantageously tailored dependent on the particular portion to which it is applied.

The above described apparatus and method may advantageously be implemented as part of system that located an impact event (e.g. on the aircraft). The above described apparatus and method may advantageously be used to corroborate a determined impact location.

Apparatus, including the processor, for implementing the above arrangement, and performing the method steps described above, may be provided by configuring or adapting any suitable apparatus, for example one or more computers or other processing apparatus or processors, and/or providing additional modules. The apparatus may comprise a computer, a network of computers, or one or more processors, for implementing instructions and using data, including instructions and data in the form of a computer program or plurality of computer programs stored in or on a machine readable storage medium such as computer memory, a computer disk, ROM, PROM etc., or any combination of these or other storage media.

It should be noted that certain of the process steps depicted in the flowcharts of FIGS. 3 and 4 and described above may be omitted or such process steps may be performed in differing order to that presented above and shown in the Figures. Furthermore, although all the process steps have, for convenience and ease of understanding, been depicted as discrete temporally-sequential steps, nevertheless some of the process steps may in fact be performed simultaneously or at least overlapping to some extent temporally.

In the above embodiments, the above described detector and method of implementing the detector are used on an unmanned aircraft. However, in other embodiments the detector and method are used on a different entity, for example, a different type of vehicle (e.g. a manned aircraft, or manned or unmanned land-based vehicle), or other structure (e.g. the blades of a wind turbine).

In the above embodiments, the sensor is a broadband, non-resonant piezoelectric sensor. However, in other embodiments, the sensor is a different appropriate type of sensor, for example, a fibre optic sensor capable of passively detecting dynamic strain.

In the above embodiments, the sensor is bonded to a surface of the portion of the aircraft. However, in other embodiments, the sensor is coupled to the portion in a different appropriate way. For example, in other embodiments the sensor is embedded into the composite material.

In the above embodiments, the detector comprises (and the method is implemented using a signal from) a single sensor. However, in other embodiments, a plurality of one or more different types of sensor is used.

The use of more than one sensor advantageously tends to provide that impacts can be detected (and damaging impacts be disambiguated from non-damaging impacts) over a wider area.

Furthermore, it tends to be possible to use signals from three or more sensors to determine a location for a point of impact on the portion (e.g. using a conventional triangulation process).

In other embodiments, a location for an impact is determined in a different way (e.g. using a conventional impact location technique). The synergistic combination of a location and severity of an impact tends to further reduce time and costs associated with inspection of the portion.

In the above embodiments, the portion is located on a leading edge of the aircraft. However, in other embodiments the portion is located at a different position on the aircraft/entity.

In the above embodiments, the aircraft is operated according to the method described above with reference to FIG. 3. However, in other embodiments, the aircraft may be operated in a different way that incorporates use of the detector.

In the above embodiments, in operation, the sensor measures 5 million samples per second. However, in other embodiments, the sensor makes measurements at a different rate. This rate may be advantageously specified depending on the size, shape, material, and function of the portion.

In the above embodiments, the signal received from the sensor is filtered by the processor using a band-pass filter such that frequencies within the frequency range 50-350 kHz are passed, and frequencies outside this range are attenuated. However, in other embodiments, the signal received from the sensor is filtered by the processor in a different way, e.g. using a square and low-pass filter method. For example, in other embodiments the signal received from the sensor is filtered by the processor using a 50-350 kHz hardware band-pass filter and, subsequently in software, a square and low-pass filter is applied. In other embodiments, the signal from the sensors is not filtered, e.g. a non-broadband sensor that is sensitive at approximately 50-350 kHz is used. In other embodiments, signals are filtered over a different frequency range to the 50-350 kHz range described above.

In the above embodiments, a damage rating for an impact is determined (as described above with reference to step s28 of FIG. 4). In particular, in the above embodiments, the damage rating is determined as the ratio between the absolute amplitude of the largest secondary pulse of the filtered signal and the absolute amplitude of the initial pulse of that filtered signal. However, in other embodiments, the damage rating is determined in a different appropriate way. For example, in other embodiments, the damage rating is determined as a different function of the amplitudes of the initial pulse and one or more of the secondary pulses of the filtered signal. In other embodiments, the damage rating is determined dependent on the durations of the initial pulse and one or more of the secondary pulses of the filtered signal. In other embodiments, the damage rating is determined dependent on the initial pulse and the number of secondary pulses of the filtered signal.

In other embodiments, no damage rating is determined. In such embodiments, only an indication that an impact event was damaging may be determined.

In the above embodiments, an output of the processor (e.g. a damage rating and a time of impact) is stored in the storage device for later use by an operator. However, in other embodiments, the output of the processor is used in a different way. For example, in other embodiments the output of the processor is transmitted to an operator of the aircraft (e.g. in "real-time") whilst the aircraft is airborne. In such embodiments, the operator may control or provide instructions to the aircraft based on the received processor output transmitted from the aircraft.

In other embodiments, only certain of the above described method steps are performed on the aircraft, for example, unprocessed sensor data may be stored on the aircraft. This unprocessed sensor data may then be processed by an entity that is remote from the aircraft (e.g. by the operator at the ground station when the aircraft returns to the ground station) to detect impacts and discriminate between damaging and non-damaging impacts.

The invention claimed is:

1. A method of processing measurements of an acoustic wave, the acoustic wave being within a member and caused, at least in part, by an impact to the member, the member being made of a composite material, the method comprising:
   analysing the measurements of the acoustic wave to detect an initial acoustic wave feature in the measured acoustic wave;
   analysing the measurements of the acoustic wave to determine whether or not there is one or more further acoustic wave features present in the measured acoustic wave, each of the one or more further acoustic wave features occurring in the acoustic wave after the occurrence of the initial acoustic wave feature;
   if there are no further acoustic wave features present in the measured acoustic wave, determining that the impact to the member has not changed a structure of the member;
   if there is one or more further acoustic wave features present in the measured acoustic wave, determining a value of a function of one or more of the further acoustic wave features;
   if the determined value satisfies one or more criteria, determining that the impact to the member has changed the structure of the member; and
   if the determined value does not satisfy the one or more criteria, determining that the impact to the member has not changed the structure of the member.

2. A method according to claim 1, the method further comprising:
   filtering the measurements of the acoustic wave; wherein
   the initial acoustic wave feature is a feature of the filtered measurements; and
   each of the further acoustic wave features is a feature of the filtered measurements.

3. A method according to claim 1, wherein:
   the initial acoustic wave feature is a pulse having an absolute amplitude greater than a first threshold value; and
   each of the further acoustic wave features is a further pulse having an absolute amplitude greater than the first threshold value.

4. A method according to claim 1, wherein a time period between the initial acoustic wave feature occurring in the measured acoustic wave and each of the further acoustic wave features occurring in the measured acoustic wave is greater than a first threshold time-period.

5. A method according to claim 1, wherein a time period between the initial acoustic wave feature occurring in the measured acoustic wave and each of the further acoustic wave features occurring in the measured acoustic wave is less than or equal to a second threshold time-period.

6. A method according to claim 1, wherein the function of one or more of the further acoustic wave features is a ratio between an amplitude of the initial acoustic wave feature and an amplitude of at least one of the further acoustic wave features.

7. A method according to claim 1, wherein the one or more criteria comprises a criterion that the determined value exceeds a second threshold value.

8. A method according to claim 1, the method further comprising, using measurements of the acoustic wave measured at a plurality of different points on or in the member, determining a location of the impact on the member.

9. A method according to claim 1, the method further comprising, if it is determined that the impact to the member has changed the structure of the member, outputting an indication that the structure of the member has changed.

10. A method according to claim 1, wherein the method is performed, at least in part, on an unmanned aircraft.

11. Apparatus for use with a member, the member being made of a composite material, the apparatus comprising:
   a sensor arranged to measure an acoustic wave, the acoustic wave being within the member and caused by an impact to the member; and
   one or more processors arranged to:
      analyse the measurements of the acoustic wave to detect an initial acoustic wave feature in the measured acoustic wave;
      analyse the measurements of the acoustic wave to determine whether or not there is one or more further acoustic wave features present in the measured acoustic wave;
      if there are no further acoustic wave features present in the measured acoustic wave, determine that the impact to the member has not changed a structure of the member;
      if there is one or more further acoustic wave features present in the measured acoustic wave, determine a value of a function of one or more of the further acoustic wave features;
      if the determined value satisfies one or more criteria, determine that the impact to the member has changed the structure of the member; and
      if the determined value does not satisfy the one or more criteria, determine that the impact to the member has not changed the structure of the member.

12. Apparatus according to claim 11, wherein:
   the sensor is either a piezoelectric sensor or a fibre optic sensor; and
   the sensor is either bonded to the member or embedded into the member.

13. An unmanned aircraft comprising:
   the apparatus of claim 11; and further comprising:
   the member being made of the composite material.

14. A non-transitory machine readable storage medium having instructions encoded thereon such that when executed by one or more processors cause the one or more processors to carry out a method of processing measurements of an acoustic wave, the acoustic wave being within a member made of a composite material and caused at least in part by an impact to the member, the method comprising:
   analysing the measurements of the acoustic wave to detect an initial acoustic wave feature in the measured acoustic wave;
   analysing the measurements of the acoustic wave to determine whether or not there is one or more further acoustic wave features present in the measured acoustic wave, each of the one or more further acoustic wave features occurring in the acoustic wave after the occurrence of the initial acoustic wave feature;
   if there are no further acoustic wave features present in the measured acoustic wave, determining that the impact to the member has not changed a structure of the member;
   if there is one or more further acoustic wave features present in the measured acoustic wave, determining a value of a function of one or more of the further acoustic wave features;
   if the determined value satisfies one or more criteria, determining that the impact to the member has changed the structure of the member; and
   if the determined value does not satisfy the one or more criteria, determining that the impact to the member has not changed the structure of the member.

15. A non-transitory machine readable storage medium according to claim 14, the method further comprising:
   filtering the measurements of the acoustic wave; wherein
   the initial acoustic wave feature is a feature of the filtered measurements; and
   each of the further acoustic wave features is a feature of the filtered measurements.

16. A non-transitory machine readable storage medium according to claim 14, wherein:
   the initial acoustic wave feature is a pulse having an absolute amplitude greater than a first threshold value; and
   each of the further acoustic wave features is a further pulse having an absolute amplitude greater than the first threshold value.

17. A non-transitory machine readable storage medium according to claim 14, wherein a time period between the initial acoustic wave feature occurring in the measured acoustic wave and each of the further acoustic wave features occurring in the measured acoustic wave is greater than a first threshold time-period.

18. A non-transitory machine readable storage medium according to claim 14, the method further comprising, using measurements of the acoustic wave measured at a plurality of different points on or in the member, determining a location of the impact on the member.

19. A non-transitory machine readable storage medium according to claim 14, the method further comprising, if it is determined that the impact to the member has changed the structure of the member, outputting an indication that the structure of the member has changed.

20. A non-transitory machine readable storage medium according to claim 14, wherein the method is performed, at least in part, on an unmanned aircraft.

* * * * *